United States Patent [19]

Grollier

[11] Patent Number: 5,567,701

[45] Date of Patent: Oct. 22, 1996

[54] ALKYLPOLYGLYCOSIDE AND PYRIMIDINE DERIVATIVE BASED COMPOSITION FOR INDUCING AND STIMULATING HAIR GROWTH AND/OR REDUCING HAIR LOSS

[75] Inventor: Jean F. Grollier, Paris, France

[73] Assignee: L'Oreal, Paris, France

[21] Appl. No.: 214,668

[22] Filed: Mar. 18, 1994

Related U.S. Application Data

[63] Continuation of Ser. No. 815,872, Jan. 3, 1992, abandoned, which is a continuation of Ser. No. 397,253, Aug. 23, 1989, abandoned.

[30] Foreign Application Priority Data

Aug. 25, 1988 [LU] Luxembourg ................. 87323

[51] Int. Cl.$^6$ .................. A61K 31/505; A61K 7/06; A61K 31/70
[52] U.S. Cl. .................. 514/256; 424/70.1; 514/25; 514/70; 514/781; 514/880; 514/881; 514/888
[58] Field of Search ................. 514/25, 70, 888, 514/881, 781, 256

[56] References Cited

U.S. PATENT DOCUMENTS

| | | | |
|---|---|---|---|
| 4,765,976 | 8/1988 | Grollier et al. | 424/881 |
| 4,820,512 | 4/1989 | Grollier | 424/70 |
| 4,871,839 | 10/1989 | Gibson | 424/880 |

FOREIGN PATENT DOCUMENTS

| | | | |
|---|---|---|---|
| 2602421 | 2/1988 | France | 424/70 |
| 3615396 | 11/1987 | Germany | 424/70 |
| 38314 | 2/1985 | Japan | 514/880 |
| 2128627 | 5/1984 | United Kingdom | 424/47 |

OTHER PUBLICATIONS

MacKenzie 1962, *A New Dictionary of Chemistry*, 240 and 241 and 244.

*Primary Examiner*—Shelley A. Dodson
*Attorney, Agent, or Firm*—Jacobson, Price, Holman & Stern, PLLC

[57] ABSTRACT

A composition for inducing and stimulating hair growth and/or reducing hair loss comprises at least one alkylpolyglycoside and at least one compound having formula (I) in a physiologically acceptable medium.

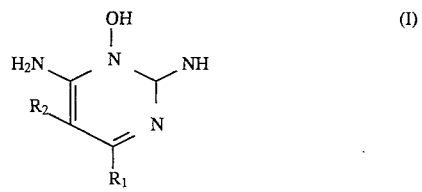

In compound (I), $R_1$ represents the group

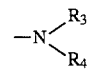

where in $R_3$ and $R_4$ may be selected from hydrogen, alkyl, alkenyl or cycloalkyl. $R_3$ and $R_4$ may also form a heterocycle with the nitrogen atom to which they are bonded. The heterocycle may be an aziridinyl, azetidinyl, pyrrolidinyl, piperidinyl, hexahydroazepinyl, heptamethyleneimine, octamethyleneimine, morpholine or 4-low alkylpiperazidinyl group. These heterocycles may be substituted at the carbon atoms by one to three alkyl, hydroxy or alkoxy groups. $R_2$ is selected from hydrogen, alkyl, alkenyl, alkylalkoxy, cycloalkyl, aryl, alkylaryl, arylalkyl, alkylarylalkyl, alkoxyarylalkyl and/or haloarylalkyl. The physiologically acceptable acid addition salts of the compound may also be used.

16 Claims, No Drawings

ALKYLPOLYGLYCOSIDE AND PYRIMIDINE DERIVATIVE BASED COMPOSITION FOR INDUCING AND STIMULATING HAIR GROWTH AND/OR REDUCING HAIR LOSS

This application is a continuation of application Ser. No. 07/815,872, filed Jan. 3, 1992, abandoned, which is a continuation of application Ser. No. 07/397,253, filed Aug. 23, 1989, abandoned.

BACKGROUND OF THE INVENTION

1. Field of the Invention

The present invention concerns a composition for inducing and stimulating hair growth and/or reducing its loss containing, in combination, at least one pyrimidine derivative and at least one alkylpolyglycoside surfactant.

Man has about 100 000 to 150 000 hairs on the head and a daily loss of 50 to 100 hairs is normal. Maintaining a head of hair is essentially dependent on a pilary cycle during which the hair is formed, grows and then falls out before being replaced by a new hair growing from the same follicle.

Three phases occur during the pilary cycle: the anagenous, catagenous and telogenous phases.

During the first or anagenous phase the hair undergoes a period of active growth associated with intense metabolic activity in the root.

The second or catagenous phase is transitory and characterised by a slowing down of metabolic activity. During this phase the hair undergoes involution, the follicle atrophies and its dermal implantation appears higher and higher.

The final or telogenous phase corresponds to a rest period for the follicle and the hair finally falls out, pushed out by a new hair in its anagenous phase.

This permanent renewal process undergoes a natural evolution during ageing whereby the hair becomes finer and the cycles shorter.

Alopecia occurs when this physical renewal process is accelerated or perturbed, ie growth phases are shortened, passage of hair into the telogenous phase speeds up and hair falls out more frequently. Successive growth cycles result in finer and finer, shorter and shorter hair, gradually resulting in unpigmented down. This phenomenon may result in baldness.

Several factors, eg alimentary, endocrinal or nervous factors, may affect the pilary cycle and result in more or less pronounced alopecia.

Variations in the different phases may be determined using a trichogram, in particular a phototrichogram.

For several years, the cosmetics and pharmaceuticals industries have sought compositions which will cure or reduce alopecia, particularly ones which will induce or stimulate hair growth or reduce hair loss.

2. Description of the Prior Art

In this respect compositions such as 6-amino -1,2-dihydro-1-hydroxy-2-imino-4-piperidinopyrimidine and its derivatives have already been used. Such compositions are described in U.S. Pat. No. 4,139,619 in particular.

In order to improve the efficacy of compositions containing pyrimidic derivatives, a composition has been sought which is tolerated well and contains pyrimidine derivative(s) which can remain in contact with the scalp over a prolonged period without being rinsed away, to encourage penetration of the active substance into the horny layer.

In this regard the applicant has discovered that by using an alkylpolyglycoside in combination with the pyrimidine derivatives it is possible to improve the efficacy of the composition in inducing and stimulating hair growth and reducing hair loss.

Combinations of the two compounds can produce compositions which are more efficaceous than those previously known and which can be used in a manner which is particularly easy and appropriate for application of active ingredients.

Use of an alkylpolyglycoside in combination with the pyrimidine derivative also allows remarkably easy elimination of the composition simply by rinsing.

The applicant has also established that the composition has good storage properties.

A composition according to the invention is also cosmetically suitable and does not cause irritation of the scalp even after prolonged contact without rinsing.

An object of the invention, therefore, is to provide a novel alkylpolyglycoside and pyrimidine derivative based composition to induce and stimulate hair growth and/or reduce its loss.

Another object of the invention is to provide pharmaceutical compositions for topical application based on this composition.

A further object of the invention is to provide a cosmetic hair and scalp treatment method using this composition.

Further objects of the invention will become clear from the following description and examples.

SUMMARY OF THE INVENTION

A composition according to the invention for inducing and stimulating hair growth and/or reducing hair loss comprises, in a physiologically acceptable medium, at least one alkylpolyglycoside and at least one compound having formula:

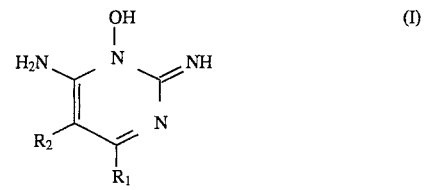

wherein
$R_1$ represents the group

and wherein:
$R_3$ and $R_4$ may be selected from hydrogen, an alkyl group preferably containing one to four carbon atoms, an alkenyl, alkylaryl or cycloalkyl group in which the alkyl portion is a lower alkyl radical;
$R_3$ and $R_4$ may also form a heterocycle with the nitrogen atom to which they are bonded, said heterocycle being selected from the following groups: aziridinyl, azetidinyl, pyrrolidinyl, piperidinyl, hexahydroazepinyl, heptamethyleneimine, octamethyleneimine, morpholine and low 4-(lower alkyl)piperazidinyl, the heterocyclic groups also being substituted at the carbon atoms by one to three lower alkyl, hydroxy or alkoxy groups;

$R_2$ is selected from hydrogen or an alkyl, alkenyl, alkylalkoxy, cycloalkyl, aryl, alkylaryl, arylalkyl, alkylarylalkyl, alkoxyarylalkyl and haloarylalkyl group, the alkyl portion of which is a lower alkyl radical, and cosmetically or pharmaceutically acceptable addition salts of associated acids.

In formula (I), alkyl or alkoxy preferably designates a group having one to four carbon atoms; alkenyl preferably designates a group having two to five carbon atoms and aryl preferably designates phenyl.

Particularly preferred compounds having formula (I) are those wherein $R_2$ designates hydrogen and $R_1$ represents the group

where $R_3$ and $R_4$ form a piperidinyl ring, as well as their salts, for example the sulfate.

A particularly preferred compound is 6-amino-1,2-dihydro-1-hydroxy-2-imino-4-piperidinopyrimidine or "Minoxidil".

Alkylpolyglycosides used according to the invention have formula (II):

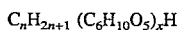   (II)

or correspond to the diagrammatic structure (III):

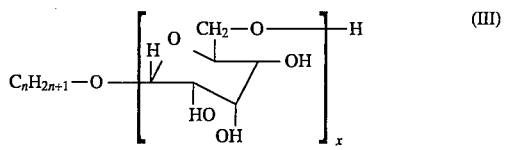   (III)

wherein:
n is an integer between 8 and 15,
x is an integer from 1 to 10.

Such products are sold by HORIZON CHEMICAL under the trade name APG.

A particularly preferred product has formula (II) wherein:
n is between 8 and 11, and
x is between 1 and 10.

Such a product is marketed by HORIZON CHEMICAL under the name APG 300 or APG 500 as an aqueous solution containing 50% active material.

The pyrimidine derivative of formula (I) is used in compositions according to the invention in a proportion of 0.05 to 6% by weight with respect to total composition weight, preferably 0.1 to 3% and advantageously 0.5 to 2%.

The alkylpolyglycoside surfactant is used in a proportion of 1 to 30% by weight with respect to total composition weight, preferably 5 to 15%.

The physiologically acceptable medium is one which is appropriate for cosmetic or pharmaceutical use and may be an aqueous medium or a mixture of water and a cosmetically or pharmaceutically acceptable solvent. It may be thickened.

The following solvents may particularly be used: $C_1$ to $C_4$ low alcohols such as ethanol, isopropanol and tert-butanol; alkyleneglycols such as propyleneglycol and alkylethers of mono- and dialkyleneglycol eg ethyleneglycol monoethylether, propyleneglycol monomethylether and diethyleneglycol monoethylether.

When used the aqueous medium, solvents are present in a proportion of 0.5 to 80% by weight with respect to total composition weight.

Known thickening agents may be used, particularly (but not exclusively): the diethanolamide of copra acids, heteropolysaccharides such as xanthane gum or scleroglucanes, cellulose derivatives and reticulated or non-reticulated acrylic polymers and polyethyleneglycols and their derivatives.

These thickeners are preferably used in a proportion of 0.1 to 6% by weight with respect to total composition weight.

These compositions may also contain ingredients normally employed in cosmetic or pharmaceutical compositions, such as preservatives, complexing agents, dyes, acidifying or alkalizing agents, perfumes or polymers.

The pH of the compositions lies between 4 and 9, preferably between 7 and 8.5.

These compositions may be packaged in aerosols. A method for the treatment of hair loss and/or stimulating hair growth principally consists in applying a composition as hereinbefore defined to alopecic areas of the scalp and hair, leaving it in contact therewith for several hours and, if necessary, rinsing it out.

The composition may, for example, be applied in the evening, left on overnight and shampooed out the following morning, or the hair could be washed again with more composition and left for a few minutes before rinsing out.

It has been observed that the inventive composition is particularly effective when applied as a capillary lotion, either as a rinse or as a shampoo.

The inventive method has the characteristics of a therapeutic treatment for alopecia in that the composition affects biological mechanisms, particularly the pilary cycle, to correct their dysfunction.

The method also has the characteristics of a cosmetic treatment in that it can improve the hair condition.

The following examples are intended to illustrate the invention without in any way limiting its scope.

EXAMPLES OF THE INVENTION

EXAMPLE 1

A shampoo using the following composition was prepared:

| | | |
|---|---|---|
| Alkylpolyglycoside APG 300 sold by HORIZON CHEMICAL as an aqueous solution containing 50% active material (AM) | | 12.0 g AM |
| Minoxidil | | 0.5 g |
| Disodium salt of ethylenediamino tetracetic acid | | 0.2 g |
| Preservative(s) | qs | |
| Water | qsp | 100.0 g |

The shampoo was applied to the hair, massaging the scalp.

It was left for several minutes and then rinsed out and the hair was then dried.

EXAMPLE 2

A lotion having the following composition was prepared:

| | | |
|---|---|---|
| Alkylpolyglycoside APG 300 sold by HORIZON CHEMICAL as an aqueous solution containing 50% active material (AM) | | 5.0 g AM |
| Minoxidil | | 0.5 g |
| Ethanol | | 15.0 g |
| Water | qsp | 100.0 g |

The lotion was applied to the scalp, left for 30 minutes and then rinsed out.

EXAMPLE 3

A capillary solution having the following composition was prepared:

| | | |
|---|---|---|
| Alkylpolyglycoside APG 300 sold by HORIZON CHEMICAL as an aqueous solution containing 50% active material (AM) | | 5.0 g AM |
| Minoxidil | | 0.5 g |
| Propyleneglycol monomethylether | | 20.0 g |
| Preservative(s) | qs | |
| Water | qsp | 100.0 g |

The lotion was applied to the scalp, left for 30 minutes and then rinsed out.

EXAMPLE 4

A shampoo having the following composition was prepared:

| | | |
|---|---|---|
| Alkylpolyglycoside APG 300 sold by HORIZON CHEMICAL as an aqueous solution containing 50% active material (AM) | | 15.0 g AM |
| Minoxidil | | 0.5 g |
| Diethanolamide of copra acids | | 5.0 g |
| Disodium salt of ethylenediamino tetracetic acid | | 0.2 g |
| Water | qsp | 100.0 g |

This composition was shampooed in and rinsed out and the hair was then dried.

EXAMPLE 5

A capillary lotion having the following composition was prepared:

| | | |
|---|---|---|
| Alkylpolyglycoside APG 350 sold by HORIZON CHEMICAL as an aqueous solution containing 50% active material (AM) | | 6.0 g AM |
| Minoxidil | | 0.15 g |
| Ethanol | | 29.84 g |
| Complexing agent | qs | |
| Water | qsp | 100.0 g |

This lotion was applied to alopecic areas of the scalp but not rinsed out.

EXAMPLE 6

A GEL shampoo having the following composition was prepared:

| | | |
|---|---|---|
| Alkylpolyglycoside (APG 500) sold by HENKEL under the trade name MERGITAL CG 60 as an aqueous solution containing 60% active material (AM) | | 13.0 g AM |
| Minoxidil | | 0.5 g |
| Thickener: PEG derivative | | 0.75 g |
| Preservatives, complexing agent | qs | |
| Water | qsp | 100.0 g |

EXAMPLE 7

A MOUSSE shampoo having the following composition was prepared:

| | | |
|---|---|---|
| Alkylpolyglycoside (APG 500) sold by HENKEL under the trade name MERGITAL CG 60 as an aqueous solution containing 60% active material (AM) | | 13.0 g AM |
| Minoxidil | | 0.15 g |
| Preservatives, complexing agent | qs | |
| Water | qsp | 100.0 g |
| Aerosol preparation: | | 95.0 g |
| Above composition | | |
| Ternary mixture of N-butane, 55% butane and propane sold by ELF AQUITANE under the trade name AEROGAZ 3.2 N | | 5.0 g |

EXAMPLE 8

A shampoo having the following composition was prepared:

| | | |
|---|---|---|
| Alkylpolyglycoside APG 500 sold by HORIZON CHEMICAL as an aqueous solution containing 50% active material (AM) | | 10.0 g |
| Minoxidil | | 0.25 g |
| Complexing agent | qs | |
| Water | qsp | 100.0 g |

There is claimed:

1. An improved composition for inducing and stimulating hair growth and/or reducing hair loss, comprising in a physiologically acceptable medium an effective concentration of one active pyrimidine compound having the formula

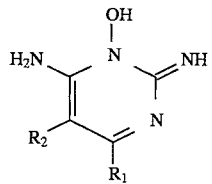

(I)

or a physiologically acceptable acid addition salt thereof, wherein:

$R_1$ represents a group having the formula

in which $R_3$ and $R_4$ are selected from the group consisting of hydrogen, lower alkyl, alkenyl, alkylaryl and cycloalkyl in which the alkyl portion is a $C_1$-$C_4$ alkyl radical, or $R_3$ and $R_4$ with the nitrogen to which they are each bound form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidinyl, hexahydroazepinyl, heptamethylenimino, octamethyleneimino, morpholino and 4-(lower alkyl)piperazinyl;

$R_2$ is selected from the group consisting of hydrogen, $C_1$-$C_4$ alkyl, alkenyl, alkoxyalkyl, cycloalkyl, aryl, alkylaryl, arylalkyl, alkylarylalkyl, alkoxyarylalkyl and haloarylalkyl, the alkyl portion of which is a lower alkyl radical; wherein the improvement is due to the addition of an effective concentration of one alkylpolyglycoside selected from the group consisting of compounds of formula (III):

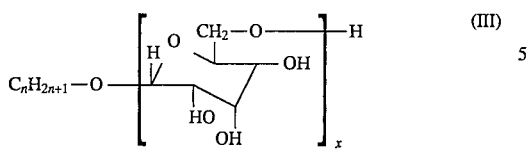

in which n is an integer between 8 and 15 and x is an integer between 1 and 10, so that the penetration of the pyrimidine compound of formula (I) into the corneal layer is encouraged and the efficiency of the said composition is substantially increased.

2. The composition of claim 1, wherein $R_2$ is hydrogen and $R_3$ and $R_4$ form a piperidinyl heterocyclic group or a salt thereof.

3. The composition of claim 2, wherein the compound of formula (I) is 6-amino-1,2-dihydro-1-hydroxy-2-imino-4-piperidinopyrimidine.

4. The composition of claim 1, wherein n is between 8 and 11 and x is between 1 and 10.

5. The composition of claim 1, wherein the concentration of said compound of formula (I) is 0.05 to 6% by weight with respect to the total weight of the composition.

6. The composition of claim 1, wherein the concentration of said alkylpolyglycoside is 1 to 30% by weight with respect to the total weight of the composition.

7. The composition of claim 1, wherein said physiologically acceptable medium is cosmetically and pharmaceutically acceptable and is selected from the group of media consisting of water, mixtures of water and a solvent, mixtures of water and a thickening agent and mixtures of water, a solvent and a thickening agent.

8. The composition of claim 1, wherein said medium includes a solvent and wherein the concentration of said solvent is 0.5 to 80% by weight with respect to the total weight of said composition.

9. The composition of claim 1, further comprising at least one thickening agent at a concentration of 0.1 to 6% by weight with respect to the total weight of said composition.

10. The composition of claim 5, wherein the concentration of said at least one pyrimidine compound of formula (I) is 0.1 to 3% by weight.

11. The composition of claim 5, wherein the concentration of said alkylpolyglycoside is 5 to 15% by weight.

12. A method for cosmetically treating hair, comprising applying to the hair or scalp an effective amount of a composition that contains, in a physiologically acceptable medium, (a) an effective concentration of at least one alkylpolyglycoside selected from the group consisting of compounds of formula (III):

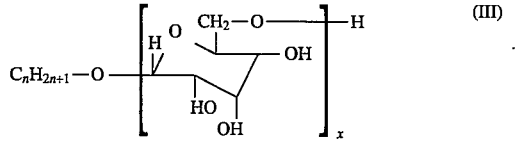

in which n is an integer between 8 and 15 and x is an integer between 1 and 10; and (b) an effective concentration of at least one active pyrimidine compound having the formula:

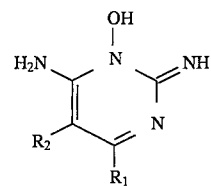

or a physiologically acceptable acid addition salt thereof, wherein $R_1$ represents a group having the formula

in which $R_3$ and $R_4$ are selected from the group consisting of hydrogen, $C_1$-$C_4$ alkyl, alkenyl, alkylaryl and cycloalkyl in which the alkyl portion is a lower alkyl radical, or $R_3$ and $R_4$ with the nitrogen to which they are each bound form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidinyl, hexahydroazepinyl, heptamethylenimino, octamethyleneimino, morpholino and 4-(lower alkyl)piperazinyl;

$R_2$ is selected from the group consisting of hydrogen, $C_1$-$C_4$ alkyl, alkenyl, alkoxyalkyl, cycloalkyl, aryl, alkylaryl, arylalkyl, alkylarylalkyl, alkoxyarylalkyl and haloarylalkyl, the alkyl portion of which is a lower alkyl radical; and said amount and concentrations are effective, when used in said composition, for inducing and stimulating the growth of hair and/or reducing its loss by encouraging the rate of penetration of said active pyrimidine compound into the corneal layer.

13. The method of claim 12, further comprising rinsing the hair and scalp after said composition has been in contact with the hair or scalp for a time sufficient for said composition to penetrate into the corneal layer.

14. An improved composition for treating alopecia, comprising, in a physiologically acceptable medium, an effective concentration of one pyrimidine compound having the formula:

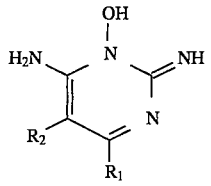

or a physiologically acceptable acid addition salt thereof, wherein:

$R_1$ represents a group having the formula

in which $R_3$ and $R_4$ are selected from the group consisting of hydrogen, $C_1$-$C_4$ alkyl, alkenyl, alkylaryl and cycloalkyl in which the alkyl portion is a lower alkyl radical, or $R_3$ and $R_4$ with the nitrogen to which they are each bound form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidinyl, hexahydroazepinyl, heptamethylenimino, octamethyleneimino, morpholino and 4-(lower alkyl)piperazinyl;

R$_2$ is selected from the group consisting of hydrogen, C$_1$-C$_4$ alkyl, alkenyl, alkoxyalkyl, cycloalkyl, aryl, alkylaryl, arylalkyl, alkylarylalkyl, alkoxyarylalkyl and haloarylalkyl, the alkyl portion of which is a lower alkyl radical;

wherein the improvement is due to the addition of an effective concentration of one alkylpolyglycoside selected from the group consisting of compounds of formula (III):

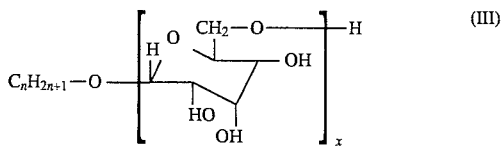

(III)

in which n is an integer between 8 and 15 and x is an integer between 1 and 10 so that the penetration of the pyrimidine compound of formula (I) is encouraged and the efficiency of the said composition is improved.

15. A method for treating alopecia, comprising applying to the hair or scalp an effective amount of a composition that contains, in a physiologically acceptable medium, (a) an effective concentration of at least one alkylpolyglycoside selected from the group consisting of compounds of formula (III):

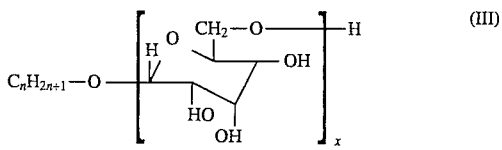

(III)

in which n is an integer between 8 and 15 and x is an integer between 1 and 10; and (b) an effective concentration of at least one pyrimidine compound having the formula:

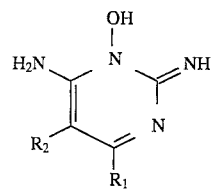

(I)

or a physiologically acceptable acid addition salt thereof, wherein:

R$_1$ represents a group having the formula

in which R$_3$ and R$_4$ are selected from the group consisting of hydrogen, C$_1$-C$_4$ alkyl, alkenyl, alkylaryl and cycloalkyl in which the alkyl portion is a lower alkyl radical, or R$_3$ and R$_4$ with the nitrogen to which they are each bound form a heterocyclic group, which is unsubstituted or is substituted on the carbon atoms with one to three lower alkyl, hydroxy, or alkoxy, and which is selected from the group consisting of aziridinyl, azetidinyl, pyrrolidinyl, piperidinyl, hexahydroazepinyl, heptamethylenimino, octamethyleneimino, morpholino and 4-(lower alkyl)piperazinyl;

R$_2$ is selected from the group consisting of hydrogen, C$_1$-C$_4$ alkyl, alkenyl, alkoxyalkyl, cycloalkyl, aryl, alkylaryl, arylalkyl, alkylarylalkyl, alkoxyarylalkyl and haloarylalkyl, the alkyl portion of which is a lower alkyl radical; and said amount and concentrations are effective, when used in said composition, for treating alopecia by encouraging the rate of penetration of said active pyrimidine compound of formula (I) into the corneal layer.

16. The method of claim 15, further comprising rinsing the hair and scalp after said composition has been in contact with the hair or scalp for a time sufficient for said composition to penetrate into corneal layer.

* * * * *